US007016466B2

United States Patent
Rinaldi et al.

(10) Patent No.: US 7,016,466 B2
(45) Date of Patent: *Mar. 21, 2006

(54) AUTOMATIC X-RAY DETECTION FOR INTRA-ORAL DENTAL X-RAY IMAGING APPARATUS

(75) Inventors: Gerardo Rinaldi, Milan (IT); Venturino Gianfranco, Milan (IT); Giuseppe Rotondo, Milan (IT)

(73) Assignee: Gendex Corporation, Washington, DC (US)

(*) Notice: Subject to any disclaimer, the term of this patent is extended or adjusted under 35 U.S.C. 154(b) by 181 days.

This patent is subject to a terminal disclaimer.

(21) Appl. No.: 10/871,724

(22) Filed: Jun. 18, 2004

(65) Prior Publication Data

US 2004/0228452 A1 Nov. 18, 2004

Related U.S. Application Data

(63) Continuation of application No. 09/754,663, filed on Jan. 4, 2001, now Pat. No. 6,775,351.
(60) Provisional application No. 60/179,639, filed on Feb. 2, 2000.

(51) Int. Cl.
*H05G 1/64* (2006.01)

(52) U.S. Cl. .................. 378/98.8; 378/108; 250/370.09
(58) Field of Classification Search ................ 378/98.8, 378/108, 19, 189, 191, 97, 98.7; 250/370.09, 250/370.05
See application file for complete search history.

(56) References Cited

U.S. PATENT DOCUMENTS

| 3,894,235 A | 7/1975 | Franke |
| 3,911,273 A | 10/1975 | Franke |

(Continued)

FOREIGN PATENT DOCUMENTS

| DE | 42 38 263 | 11/1992 |
| DE | 44 33 545 | 10/1994 |

(Continued)

OTHER PUBLICATIONS

E.R. Fossum, R.H. Nixon, D. Schick, "A 37×28mm 600k–Pixel CMOS APS Dental X–Ray Camera–On–A–Chip With Self–Triggered Readout", 1998 IEEE International Solid State Circuits Conference, 1998, ISSC98/Session11/Image Sensors/Paper FA 11,3.

(Continued)

*Primary Examiner*—Craig E. Church
*Assistant Examiner*—Irakli Kiknadze
(74) *Attorney, Agent, or Firm*—McNees Wallace & Nurick LLC; Brian T. Sattizahn

(57) ABSTRACT

An apparatus and method used in intra-oral dental x-ray imaging equipment provides automatic detection of the x-ray emission in order to obtain timely transition to the image integration and acquisition phase with high level of rejection of false triggering induced by blemish defects of the image sensor or by variations of the ambient and temperature conditions. A solid state imager, such as a CCD image sensor, is continually clocked during the standby phase prior to irradiation from an X-ray source, so providing on same time an output signal proportional to the accumulated dark current and the continuous removal of the same. A control unit analyses the output signal of the imager, detects the variation caused by the start of the x-ray emission using appropriate threshold levels, and automatically triggers the imager to the image integration and acquisition phases. Based on memorised maps of the imager blemish defects, and continually monitored variations of the imager output signal, the control unit will reject false triggering due to imager defects or variations of the ambient and temperature conditions.

19 Claims, 2 Drawing Sheets

U.S. PATENT DOCUMENTS

| | | |
|---|---|---|
| 3,974,385 A | 8/1976 | Grim |
| 3,987,281 A | 10/1976 | Hodes |
| 3,991,314 A | 11/1976 | Schmitman et al. |
| 4,021,672 A | 5/1977 | Franke |
| 4,061,920 A | 12/1977 | Mollendorf et al. |
| 4,070,578 A | 1/1978 | Timothy et al. |
| 4,097,741 A | 6/1978 | Pfeiler et al. |
| 4,104,531 A | 8/1978 | Weiss |
| 4,158,138 A | 6/1979 | Hellstrom |
| 4,160,906 A | 7/1979 | Daniels et al. |
| 4,160,997 A | 7/1979 | Schwartz |
| 4,188,537 A | 2/1980 | Franke |
| 4,247,780 A | 1/1981 | Webber et al. |
| 4,259,582 A | 3/1981 | Albert |
| 4,352,987 A | 10/1982 | Hayashi et al. |
| 4,454,606 A | 6/1984 | Relihan |
| 4,475,224 A | 10/1984 | Grassme |
| 4,486,896 A | 12/1984 | Richter et al. |
| 4,495,632 A | 1/1985 | Nakano |
| 4,501,010 A | 2/1985 | Grassme |
| 4,589,121 A | 5/1986 | Makino |
| 4,641,331 A | 2/1987 | Makino et al. |
| 4,675,888 A | 6/1987 | Gastrin |
| 4,741,007 A | 4/1988 | Virta et al. |
| 4,783,793 A | 11/1988 | Virta et al. |
| 4,797,905 A | 1/1989 | Ochmann et al. |
| 4,811,372 A | 3/1989 | Doebert et al. |
| 4,813,060 A | 3/1989 | Heubeck et al. |
| 4,815,115 A | 3/1989 | Nieminen et al. |
| 4,823,369 A | 4/1989 | Guenther et al. |
| 4,847,881 A | 7/1989 | Heubeck |
| 4,856,038 A | 8/1989 | Guenther et al. |
| 4,878,234 A | 10/1989 | Pfeiffer et al. |
| 4,905,265 A | 2/1990 | Cox et al. |
| 4,930,146 A | 5/1990 | Flakas et al. |
| 4,980,905 A | 12/1990 | Meccariello |
| 4,985,907 A | 1/1991 | Moteni |
| 4,995,062 A | 2/1991 | Schulze-Ganzlin et al. |
| 5,005,195 A | 4/1991 | Lanza et al. |
| 5,018,177 A | 5/1991 | McDavid et al. |
| 5,043,582 A | 8/1991 | Cox et al. |
| 5,090,040 A | 2/1992 | Lanza et al. |
| 5,090,047 A | 2/1992 | Angotti et al. |
| 5,093,852 A | 3/1992 | Nishikawa et al. |
| 5,195,114 A | 3/1993 | Sairenji et al. |
| 5,214,686 A | 5/1993 | Webber |
| 5,267,296 A | 11/1993 | Albert |
| 5,293,312 A | 3/1994 | Waggener |
| 5,386,448 A | 1/1995 | Tammisalo et al. |
| D355,964 S | 2/1995 | Nelvig |
| 5,425,065 A | 6/1995 | Jarvenin |
| 5,434,418 A | 7/1995 | Schick |
| 5,454,022 A | 9/1995 | Lee et al. |
| 5,473,660 A | 12/1995 | Bastiaens et al. |
| 5,490,197 A | 2/1996 | Albert et al. |
| 5,511,106 A | 4/1996 | Doebert et al. |
| 5,513,252 A | 4/1996 | Blaschka et al. |
| 5,519,437 A | 5/1996 | Nelvig |
| 5,519,751 A | 5/1996 | Yamamoto et al. |
| 5,541,974 A | 7/1996 | Sklebitz |
| 5,579,366 A | 11/1996 | Doebert et al. |
| 5,583,905 A | 12/1996 | Nishiki et al. |
| 5,600,699 A | 2/1997 | Suzuki et al. |
| 5,602,896 A | 2/1997 | Diepstraten |
| 5,608,455 A | 3/1997 | Oda |
| 5,617,462 A | 4/1997 | Spratt |
| 5,625,662 A | 4/1997 | Toth et al. |
| 5,640,018 A | 6/1997 | Suzuki et al. |
| 5,663,998 A | 9/1997 | Suzuki et al. |
| 5,664,001 A | 9/1997 | Tachibana et al. |
| 5,668,375 A | 9/1997 | Petrick et al. |
| 5,677,940 A | 10/1997 | Suzuki et al. |
| 5,694,448 A | 12/1997 | Morcom |
| 5,742,659 A | 4/1998 | Atac et al. |
| 5,744,806 A | 4/1998 | Frojd |
| 5,751,783 A | 5/1998 | Granfors et al. |
| 5,757,011 A | 5/1998 | Whitebook et al. |
| 5,773,832 A | 6/1998 | Sayed et al. |
| 5,784,429 A | 7/1998 | Arai |
| 5,796,430 A | 8/1998 | Katoh et al. |
| 5,812,191 A | 9/1998 | Orava et al. |
| 5,828,720 A | 10/1998 | Syrjanen |
| 5,828,721 A | 10/1998 | Schulze-Ganzlin et al. |
| 5,864,146 A | 1/1999 | Karellas |
| 5,892,227 A | 4/1999 | Schieber et al. |
| 5,912,942 A | 6/1999 | Schick et al. |
| 5,923,722 A | 7/1999 | Schulz |
| 5,930,330 A | 7/1999 | Wolfe et al. |
| 5,933,471 A | 8/1999 | Kalvin |
| 5,969,360 A | 10/1999 | Lee |
| 5,974,166 A | 10/1999 | Ino et al. |
| 6,002,742 A | 12/1999 | Nelvig |
| 6,035,013 A | 3/2000 | Orava et al. |
| 6,047,042 A | 4/2000 | Khutoryansky et al. |
| 6,055,292 A | 4/2000 | Zeller et al. |
| 6,069,935 A | 5/2000 | Schick et al. |
| 6,081,739 A | 6/2000 | Lemchen |
| 6,093,019 A | 7/2000 | Morandi et al. |

FOREIGN PATENT DOCUMENTS

| | | |
|---|---|---|
| DE | 197 54 463 | 8/1997 |
| DE | 19823958 | 5/1998 |
| EP | 0 229 497 | 7/1987 |
| EP | 0 234 603 | 7/1987 |
| EP | 0 408 167 | 7/1989 |
| EP | 0 373 717 | 6/1990 |
| EP | 0 574 368 | 12/1993 |
| EP | 0 673 623 | 3/1994 |
| EP | 0 632 994 | 5/1994 |
| EP | 0 634 671 | 5/1994 |
| EP | 0 632 995 | 6/1994 |
| EP | 0 685 201 | 5/1995 |
| EP | 0 776 149 | 11/1996 |
| EP | 0756416 | 2/1997 |
| EP | 0 858 773 | 2/1998 |
| GB | 2304017 | 12/1996 |
| JP | 62 222 780 | 9/1987 |
| JP | 11188033 | 7/1999 |
| WO | WO 89/07322 | 8/1989 |
| WO | WO 90/14793 | 12/1990 |
| WO | WO 91/15786 | 10/1991 |
| WO | WO 93/23952 | 11/1992 |
| WO | WO 93/11707 | 12/1992 |
| WO | WO 93/00046 | 1/1993 |
| WO | WO 93/00649 | 1/1993 |
| WO | WO 93/14418 | 7/1993 |
| WO | WO 94/12855 | 6/1994 |
| WO | WO 96/32064 | 10/1996 |
| WO | WO 98/24059 | 6/1998 |
| WO | WO 98/56214 | 12/1998 |
| WO | WO 99/17659 | 4/1999 |
| WO | WO 99/62404 | 12/1999 |

OTHER PUBLICATIONS

J.D. Cox, D.S. Langford, D.W. Williams, "Electronic inter-oral dental x-ray imaging system employing a direct sensing CCD array", X-Ray Detector Physics and Applications II, 1993, pp. 38-47, SPIL vol. 2009.

AUTOMATIC X-RAY DETECTION FOR INTRA-ORAL DENTAL X-RAY IMAGING APPARATUS

This application is a continuation of application Ser. No. 09/754,663, filed Jan. 4, 2001, U.S. Pat. No. 6,775,351, which claims the benefit of U.S. Provisional Application 60/179,639, filed Feb. 2, 2000.

BACKGROUND OF THE INVENTION

CCD and other types of solid state imagers have got widespread use in dental and medical radiology for their ability to provide in real time x-ray images of high diagnostic value, with reduced levels of the X-ray dose imparted to the patient versus the conventional radiographic film.

In the most typical arrangement the imager is in a wait state, and requires to be triggered into an integration state as soon as the irradiation starts, where the imager clocking is suspended and the x-ray conversion charge is accumulated.

It is one desirable feature that the triggering to the integration state occurs in an automatic way, without need of connections to the x-ray generator, using as low as possible x-ray dose threshold to minimise useless x-ray dosage to the patient.

In case that such automatic triggering is adopted, adequate provision is also desirable against occurrence of false triggering, as it may be caused by variations in the image sensor output signal due to abnormal imager defects and/or variations of the ambient and temperature conditions.

For the intrinsic characteristics of the imager, usually a remarkable dark current is spontaneously generated, which is having a negative impact on the noise performance of the diagnostic image.

It is another desirable feature that appropriate technique is used to remove the generated dark current and its effects on the acquired image. It is also desirable that the method used to remove the dark current will have a minimised impact on the power consumption of the imaging system, to favour those applications where the imaging system is to be self powered from the communication port of the computer station without need of additional external power supply and cabling, and easy portability of the imaging system between different computer stations shall be provided.

Prior art automatic x-ray detection apparatus have been based on an electrical connection with the x-ray generator, where a control signal is generated synchronised with the start of the exposure, to be used by the imager to automatically switch into integration mode.

Such arrangement is clearly disadvantageous for the need of having an electrical connection with the x-ray generator.

In other prior art arrangements one or more x-ray detectors, such as photo diodes, are located close to the imaging area and are used to provide detection of the x-ray emission and switching of the imager to integration mode, by a suitable control signal sent to the control electronics. Such arrangement is inherently more expensive, although characterised by a prompt reaction time, and does not provide the collateral advantage of removing the accumulated dark current as provided by the continuous clocking and readout method.

In other prior art arrangements the imager is continuously clocked and readout during standby mode prior to irradiation, the video output signal produced by the imager is compared with a threshold level by using a comparator circuit, if the threshold level is exceeded the imager is automatically switched into integration mode. As a variation of this arrangement the threshold level may be continually adjusted to account for variations of the temperature and ambient conditions.

This arrangement is disadvantageous because it requires an external analogue circuit for the comparison and does not allow for sophisticated processing of the video output in order to prevent false triggering caused by abnormal imager defects.

SUMMARY OF THE INVENTION

The object of the invention is an automatic x-ray detection apparatus and method for x-ray digital imagers for dental and medical application, capable of producing automatic triggering of the imager to the integration mode with immediate reaction to the start of the x-ray emission, and including provision against occurrence of false triggering caused by variations in the image sensor output signal due to abnormal imager defects and/or variations of the ambient and temperature conditions.

The method adopted will ensure at the same time effective removal of the dark current spontaneously generated in the imager, with minimised impact on the power consumption of the imaging system, while the apparatus will perform its function without need of electrical connections to the x-ray generator and will use the processing power of the existing microcontroller, without need of additional comparator circuitry.

The invention is particularly advantageous for the dental and medical x-ray diagnosis, where the outlined features find immediate application, but it could also be advantageously employed in other non medical applications having similar requirements.

Herefollowing is a description in greater detail of the invention, based on the exemplary embodiment illustrated in the attached drawings.

DESCRIPTION OF DRAWINGS AND TABLES

DETAILED DESCRIPTION

Figure 1:
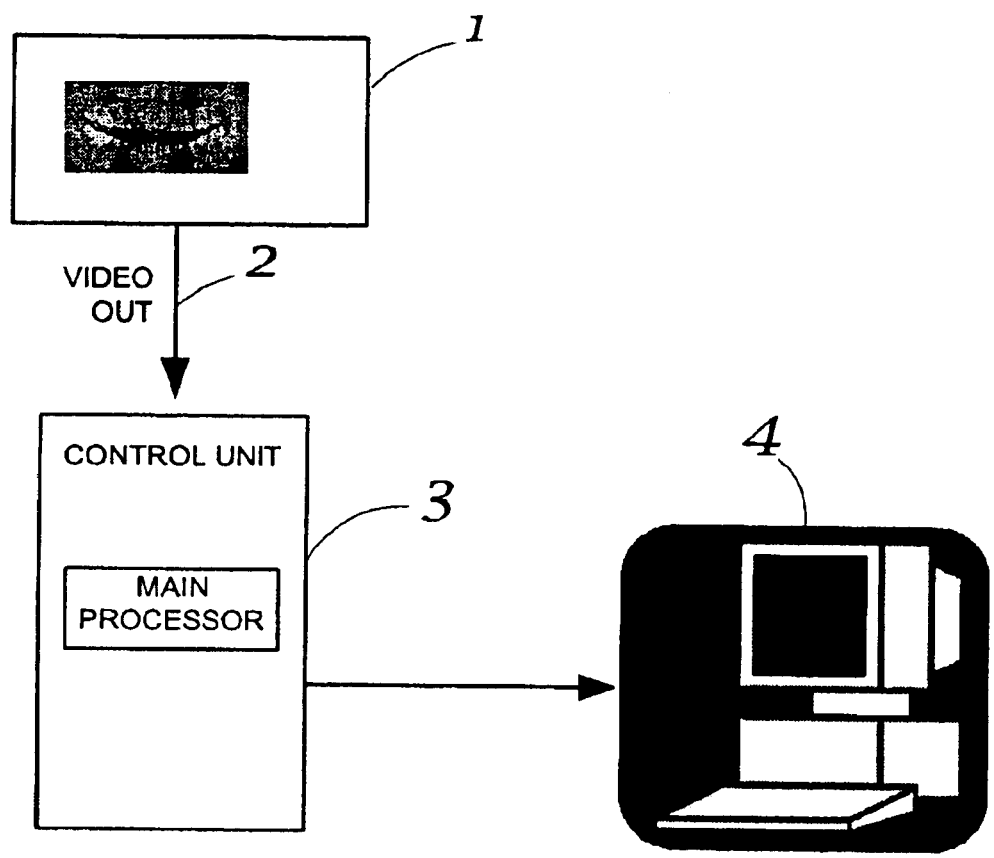
FIG. 1 is a diagram showing an exemplary system dedicated to dental application

The system illustrated in FIG. 1 is a typical x-ray diagnostic system dedicated to dental intra-oral radiography with digital image acquisition.

The x-ray source 1 is aligned with the image receptor 2 (the x-ray imager) by means of a suitable alignment device. The imager is located in the patient mouth, behind the object (tooth) to be imaged. It is connected to the control unit 3, providing imager control and image acquisition and transfer to the main processor 4 (i.e. the Personal Computer), where the diagnostic image display, processing and archive is performed.

The x-ray imager is a solid state device including a matrix of radiation sensitive pixels.

Solid state imagers, such as CCD devices, are in general exhibiting spontaneous generation of dark current, which is in turn generating a noise signal increasing, by know relations, with the temperature and with the time.

As this noise signal may significantly use the signal range of the device, it is imperative that adequate provision is taken to remove its contribution from the useful image signal.

In the proposed arrangement a continuous read out of the imager is performed during the wait time before irradiation, and the output signal is converted in digital form and analysed by the control unit, with the multiple purpose of (1) detecting variations of the output signal versus a threshold reference which can be correlated with the start of the irradiation, (2) rejecting variations of the output signal which are caused by abnormal blemish defects of the imager, (3) providing simulation of the imager temperature and accordingly correction of the threshold reference based on the actual device temperature.

The same read out process will ensure the cyclic removal of the dark current during the wait time, so minimising its influence on the latent image which will build into the imager during the integration mode.

The read out process during wait time will also adopt adequate strategy to minimise the power consumption. This will result particularly favourable in those applications where the power consumption shall be reduced to allow easy portability of the imaging system between different computer stations and self powering from the communication port of the same computer station, without need of additional external power supply and cabling.

Of course dark current will spontaneously generate during the integration and acquisition phases as well. Know methods are available to reduce this influence either by techniques to minimise the dark current generation into the solid state device, or by providing a subtraction of a dummy image build up without irradiation using similar integration time as used during the irradiation.

Figure 2:
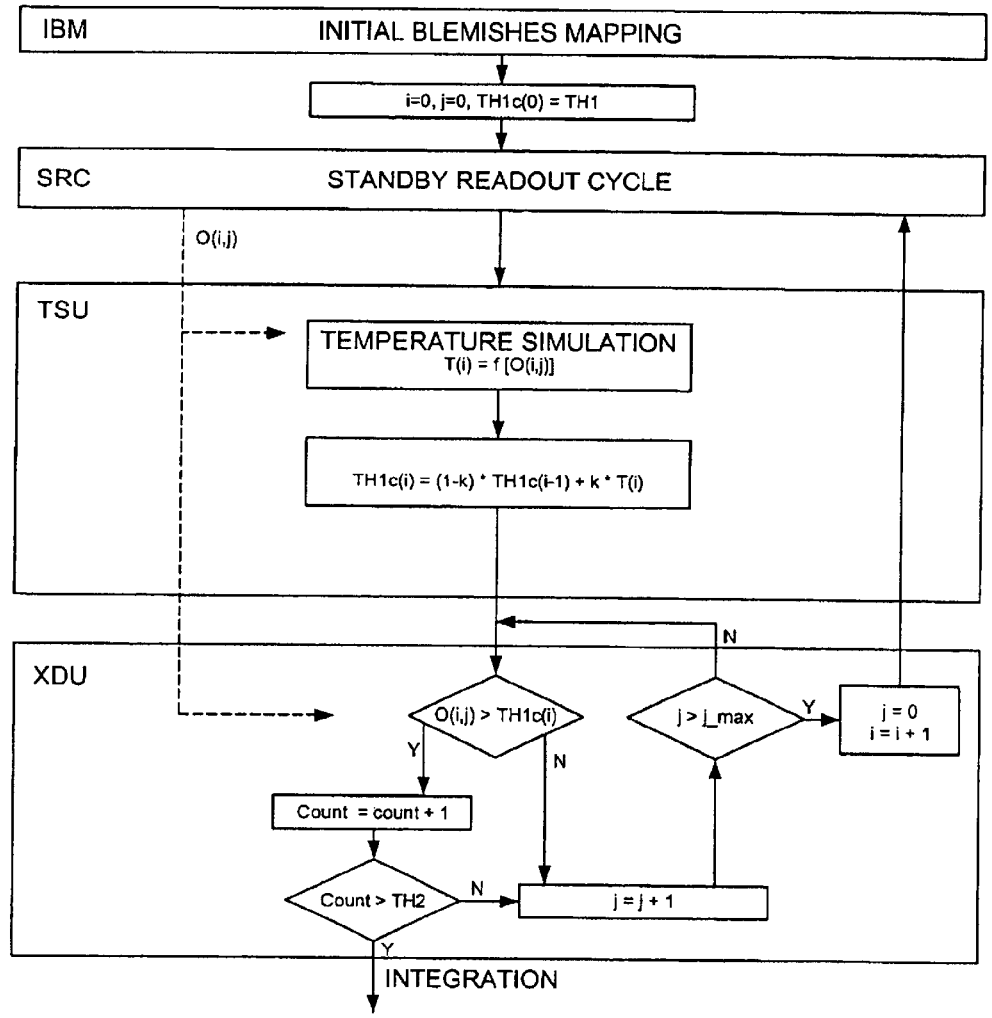
FIG. 2 is a flow chart illustrating the main apparatus functions and method.

The automatic x-ray detection apparatus incorporates several functions, which are illustrated in FIG. 2 and are described below:

IBM (Initial Blemishes Mapping).

This functional unit performs an initial read out of the whole imager pixel matrix, with the purpose of creating a map of the pixels showing blemish defect.

In a first arrangement, the output signal from each imager matrix pixel is analysed and the pixels having signal in excess of a predefined threshold reference quantity are individually recorded.

In another preferred arrangement the imager matrix may be divided into sections and within each section the pixels may be grouped and added together (so creating a super-pixel), to collect a significant signal and to reproduce the same readout policy adopted during the standby readout (see the following SRC function). The output signal from each super-pixel is analysed and, for each imager section, the super-pixels having signal in excess of a predefined threshold reference quantity are individually recorded.

It has to be noticed that, by performing such initial readout at each power on of the control unit, it is ensured the immediate recording of any new pixel blemishes which may generate into the imager device.

(a) SRC (Standby Readout Cycle).

This functional unit performs a cyclic read out of the imager matrix during the standby phase, producing the output $O(i,j)$ at each cycle $(i)$, where $j$ is index of the output element. The read out will have the consequential effect of removing at each cycle the dark current accumulated in all pixels of the matrix.

In a first arrangement, the whole imager matrix is read out pixel by pixel, and an output signal is generated referred to each individual pixel.

In a second preferred arrangement the imager matrix may be divided into sections and within each section the pixels may be grouped and added together (so creating a super-pixel), with the purpose of collecting a significant signal for the comparison. In this arrangement the output signal will be referred to each super-pixel.

As a variant of the second arrangement, it may be particularly advantageous in applications where the minimisation of the power consumption is required, such as for example CCD imagers with control electronics self powered from the USB port of a Personal Computer, to adopt a low power read out strategy, by using the reduction of the amount of the high frequency pixel shifts in the readout register, which typically provide a major contribution to the on chip power consumption. It can be achieved for example by shifting first all the lines of a section into the readout register, and then shifting all the pixels of the readout register to the output circuit. The amount of low frequency line shifts should therefore be maximised, taking also in consideration eventual limitations associated with the full-well capacity of the readout register elements.

(b) XDU (X-ray Detection Unit).

This functional unit processes the output generated by the SRC function, in order to identify the start of the irradiation and consequently generate a control signal to trigger the transition of the imager to integration mode.

In the preferred arrangement a multiple threshold will be used, with the purpose of ensuring at the same time fast response to the start of irradiation and high level of filtration of the noise components (thermal noise, dark current).

The output signal $O(i,j)$ generated by the SRC function at the cycle $(i)$ will be compared with a first threshold (TH1), to identify the pixels, or super-pixels, providing x-ray stimulated output signal. The number of such pixels will then be counted, and will be compared with a second threshold (TH2). In case that such number will exceed the second Threshold Reference (TH2), the start of irradiation will be identified and a control signal will be generated to trigger the transition of the imager to integration mode.

Output values which exceed the TH1 level, but which also correspond to pixels or super-pixels previously identified by the IBM function as blemishing, will be rejected.

In an alternative arrangement the start of irradiation may be identified by the simple detection of the first output signal exceeding the first threshold TH1. This arrangement is characterised by fast response but lower capacity of filtration of the noise components.

Another alternative arrangement may use a derivative approach, by comparing with a TH1 threshold the variation of the output signal between adjacent pixels or super-pixels. This arrangement is also characterised by fast response, but very low filtration of the noise components.

Another alternative arrangement may use an integrative approach, by integrating the output signal and comparing the integrated value with a threshold TH1. This arrangement is characterised by a slow response, but a high level of filtration of the noise components.

(c) TSU (Temperature Simulation Unit).

This functional unit performs a simulation of the imager temperature and accordingly a correction of the first Threshold Reference (TH1) value, to account for variations of the dark current related pixel (or super-pixel) signal in consequence of variations of the device temperature.

Generally the simulation $T(i)$ of the imager temperature at the cycle $(i)$ will be a function $f[O(i,j)]$ of the output $O(ij)$ generated by the SRC function at the cycle $(i)$. In the preferred arrangement the function $f[O(i,j)]$ will be the average over a consistent number of pixels, or super-pixels, which were not identified as blemishing by the IBM function.

The calculation of the Threshold Reference 1 Corrected TH1c(i) will be generally obtained as a function f[TH1c(i−1), T(i)] of the simulated temperature T(i) at the cycle (i) and of the Threshold Reference 1 Corrected TH1c(i−1) at the cycle (i−1).

In the preferred arrangement the Threshold Reference 1 Corrected TH1c(i) at the cycle (i) will be obtained by adding to the Threshold Reference 1 Corrected (TH1c) at the cycle (i−1) a term derived by the simulated temperature T(i) multiplied by a constant scaling factor(0<k<1), according to the relation $$TH1c(i)=(1-k)*TH1c(i-1)+k*T(i).$$

The preferred arrangement will provide smoothed response with higher rejection of noise terms.

Based on the functional units above, the method of this invention will be based on the following steps (refer also to the flow chart in illustration 2):

1) After switch on of the apparatus, an initial readout of the imager matrix is performed, by the IBM function, to generate a map of the pixels (or super-pixels) showing blemish defect.
2) During the standby phase, a cyclic read out of the imager matrix is performed, using the SRC function. At each cycle (i) the functional unit will generate the outputO(i,j), where (j) is the index of the element. The read out may be executed either by pixel or by super-pixel, eventually sub-dividing the imager area in sections. The read out will have the consequential effect of removing at each cycle the dark current accumulated in all pixels of the matrix.
3) The output of the SRC function is analysed by the TSU function, in order to provide a simulated value of the device temperature.

The simulated temperature value T(i) at the cycle (i) is used to calculate the Threshold Reference 1 Corrected TH1c(i) for the XDU function.

4) The output of the SRC function is also used by the XDU function, to detect the start of irradiation.

In the preferred arrangement the output signal will be compared with a first threshold 1 (TH1), to identify the pixels, or super-pixels, providing x-ray stimulated output signal. The number of such pixels will then be counted, and will be compared with a second threshold (TH2). In case that such number will exceed the second Threshold Reference (TH2), the start of irradiation will be identified and a control signal will be generated to trigger the transition of the imager to integration mode.

We claim:

1. A method for the automatic detection of the start of irradiation in an x-ray imaging system for digital radiography, the x-ray imaging system comprising an x-ray imager matrix that is electrically coupled to a control unit, the method comprising the steps of:

reading out an x-ray imager matrix to create a blemishes map of pixels or sections of the x-ray imager matrix that show blemish defects;

reading out the x-ray imager matrix to produce output elements O(i,j) at each readout cycle i, where j is the index of the output element, each output element O(i,j) corresponding to a pixel or section of the x-ray imager matrix;

comparing the output elements O(i,j) with a temperature corrected first threshold TH1c(i), wherein the temperature corrected first threshold TH1c(i) at the present readout cycle i is a function f[TH1c(i−1), T(i)] of the temperature corrected first threshold TH1c(i−1) at the previous readout cycle i−1 and a simulated temperature T(i) at the present readout cycle i;

counting the number of output elements O(i,j) that exceed the temperature corrected first threshold TH1c(i), wherein output elements O(i,j) that correspond to pixels or sections of the x-ray imager matrix which are identified as blemish defects in the blemishes map are rejected even if their corresponding output elements O(i,j) exceed the temperature corrected first threshold TH1c(i);

identifying a start of irradiation in response to a determination that the counted number of output elements O(i,j) exceeds a second threshold TH2; and repeating the steps of reading out the x-ray imager matrix to produce output elements O(i,j), comparing the output elements O(i,j) with a temperature corrected first threshold TH1c(i), counting the number of output elements O(i,j) that exceed the temperature corrected first threshold TH1c(i), and identifying a start of irradiation in response to a determination that the counted number of output elements O(i,j) exceeds a second threshold TH2, upon a determination that the counted number of output elements O(i,j) is less than a second threshold TH2.

2. The method of claim 1 wherein the simulated temperature T(i) is a function f[O(i,j)] of the output elements O(i,j) generated in the present readout cycle i.

3. The method of claim 2 wherein the simulated temperature T(i) is the average over those output elements O(i,j) that correspond to pixels or sections of the x-ray imager matrix that are not identified as blemish defects in the blemishes map.

4. The method of claim 1 wherein the step of reading out the x-ray imager matrix to produce output elements O(i,j) includes effectively removing for each readout cycle dark current accumulated in all pixels of the x-ray imager matrix.

5. The method of claim 1 wherein the step of reading out the x-ray imager matrix to create a blemishes map includes:

reading out the x-ray imager matrix pixel by pixel;

analyzing an output signal for each pixel of the x-ray imager matrix; and individually recording in the blemishes map the analyzed pixels that have an output signal greater than a predefined threshold reference quantity.

6. The method of claim 1 wherein the step of reading out the x-ray imager matrix to create a blemishes map includes:

dividing the x-ray imager matrix into sections;

binning together the pixels in each section to create a super-pixel for the section;

analyzing an output signal for each super-pixel; and individually recording in the blemishes map the analyzed super-pixels that have an output signal greater than a predefined threshold reference quantity.

7. The method of claim 1 wherein the step of reading out the x-ray imager matrix to produce output elements O(i,j) includes:

dividing the x-ray imager matrix into sections;

binning together the pixels in each section to create a super-pixel for the section; and wherein each output element O(i,j) corresponds to one super-pixel.

8. The method of claim 7 wherein the step of reading out the x-ray imager matrix to produce output elements O(i,j) further includes:

clocking into a readout register all lines of a section;

clocking out the readout register to generate an output signal for each super-pixel consisting of a column of the section.

9. The method of claim 1 wherein the calculation of the temperature corrected first threshold TH1c(i) at the readout cycle i is obtained by adding the temperature corrected first threshold TH1c(i−1) at the previous readout cycle i−1 to a term derived by the simulated temperature T(i) multiplied by a constant scaling factor k, according to the relation TH1c(i)=(1−k)*TH1c(i−1)+k*T(i).

10. The method of claim 1 wherein the step of identifying a start of irradiation in response to a determination that the counted number of output elements O(i,j) exceeds a second threshold TH2 includes identifying a start of irradiation in response to a determination that one output element O(i,j) exceeds the temperature corrected first threshold TH1c(i).

11. A method for the automatic detection of the start of irradiation in an x-ray imaging system for digital radiography, the x-ray imaging system comprising an x-ray imager matrix that is electrically coupled to a control unit, the method comprising the steps of:

reading out an x-ray imager matrix to create a blemishes map of pixels or sections of the x-ray imager matrix that show blemish defects;

reading out the x-ray imager matrix to produce output elements at each readout cycle, each output element corresponding to a pixel or section of the x-ray imager matrix;

processing the output elements using one of a derivative approach and an integration approach to obtain a plurality of processed values;

identifying a start of irradiation in response to a determination that one processed value of the plurality of processed values is greater than a temperature corrected threshold value; and repeating the steps of reading out the x-ray imager matrix to produce output elements, processing the output elements, and identifying a start of irradiation in response to a determination that each processed value of the plurality of processed values is less than the temperature corrected threshold value.

12. The method of claim 11 wherein the step of processing the output elements using one of a derivative approach and an integration approach to obtain a plurality of processed values includes the step of integrating each output element to obtain a processed value for each output element.

13. The method of claim 11 wherein the step of processing the output elements using one of a derivative approach and an integration approach to obtain a plurality of processed values includes the step of determining a variation between adjacent output elements, the variation between adjacent output elements being a processed value.

14. The method of claim 11 wherein temperature corrected threshold value is a function of the temperature corrected threshold at a previous readout cycle and a simulated temperature at a present readout cycle.

15. The method of claim 14 wherein the simulated temperature at a present readout cycle is a function of the output elements generated in the present readout cycle.

16. The method of claim 15 wherein the simulated temperature is the average over those output elements that correspond to pixels or sections of the x-ray imager matrix that are not identified as blemish defects in the blemishes map.

17. A x-ray imaging system for digital radiography comprising:

a x-ray source to provide irradiation upon command from an operator;

a x-ray imager aligned with the x-ray source, the x-ray imager comprising an imager pixel matrix; and a control system electrically coupled to the x-ray imager and being configured to automatically detect a start of irradiation, the control system comprising:

an initial blemish mapping unit, the initial blemish mapping unit being configured to readout the imager pixel matrix and create a map of the pixels showing blemish defects on startup of the x-ray imaging system;

a standby readout unit, the standby readout unit being configured to cyclically readout the imager pixel matrix and generate an output signal for each pixel of the imager pixel matrix;

a temperature simulation unit, the temperature simulation unit being configured to simulate a temperature of the x-ray imager and provide a corrected threshold reference value for determining a start of irradiation in response to the simulated temperature to account for variations in dark current in the output signals of the pixels of the imager pixel matrix resulting from variations in temperature of the x-ray imager; and a x-ray detection unit to detect a start of irradiation, the x-ray detection unit being configured to determine a start of irradiation using the corrected threshold reference value, the map of pixels showing blemish defects and the output signals for each pixel of the imager pixel matrix and generate a control signal to transition the x-ray imager to an integration mode upon the detection of a start of irradiation.

18. The x-ray imaging system of claim 17 wherein the standby readout unit is configured to effectively remove dark current accumulated in all pixels of the image pixel matrix for each readout cycle.

19. The x-ray imaging system of claim 17 wherein the x-ray detection unit is configured to determine the start of irradiation by comparing the output signal for each pixel with a corrected threshold reference value, counting the number of output signals that exceed the corrected threshold reference value, wherein output signals that correspond to pixels of the x-ray imager matrix that are identified as blemish defects in the blemishes map are rejected even if their corresponding output signals exceed the corrected threshold reference value, and identifying a start of irradiation in response to a determination that the counted number of output elements exceeds a second threshold.

* * * * *